United States Patent [19]

Kaplan

[11] Patent Number: 4,940,574
[45] Date of Patent: Jul. 10, 1990

[54] NON-AQUEOUS HIGH SPF SUNSCREEN OILS

[75] Inventor: Carl Kaplan, Memphis, Tenn.

[73] Assignee: Plough, Inc., Memphis, Tenn.

[21] Appl. No.: 289,335

[22] Filed: Dec. 22, 1988

[51] Int. Cl.$^5$ .................... A61K 7/40; A61K 7/42; A61K 7/44
[52] U.S. Cl. ........................ 424/59; 424/60; 514/873
[58] Field of Search .................. 424/59, 60

[56] References Cited

U.S. PATENT DOCUMENTS

| | | | |
|---|---|---|---|
| 2,853,423 | 9/1958 | La Via | 424/47 |
| 2,974,089 | 3/1961 | Alexander et al. | 424/59 |
| 3,185,627 | 5/1965 | Kass | 424/59 |
| 4,559,225 | 12/1985 | Fourman | 424/59 |
| 4,663,155 | 5/1987 | Murray et al. | 424/59 |
| 4,686,099 | 8/1987 | Palinczar | 424/47 |

OTHER PUBLICATIONS

DiSapio, Cosmetics & Toiletries, 1987, vol. 102, pp. 102 to 106.

*Primary Examiner*—Dale R. Ore
*Attorney, Agent, or Firm*—Henry C. Jeanette; Thomas D. Hoffman; Gerald S. Rosen

[57] ABSTRACT

Non-aqueous sunscreen oils having a high SPF value and containing a volatile oil such as a volatile silicone oil, an emollient containing esters of straight and branched chain $C_{10}$–$C_{16}$ alcohols and $C_4$–$C_{20}$ mono- or dicarboxylic acids such as tridecyl stearate and an ester of a straight or branched-chain $C_{10}$–$C_{16}$ alcohol and a tri(loweralkyl) substituted benzoic acid such as tridecyl trimellitate, esters of branched-chain $C_5$–$C_{10}$ glycols and $C_4$–$C_{20}$ mono- and dicarboxylic acid such as the diester of neopentyl glycol and decanoic acid and the diester of neopentyl glycol and octanoic acid and a sunscreening effective amount of at least two UV-B type sunscreens and at least one UV-A type sunscreen.

18 Claims, No Drawings

NON-AQUEOUS HIGH SPF SUNSCREEN OILS

BACKGROUND OF THE INVENTION

This invention relates to non-aqueous high SPF sunscreen oils containing at least one volatile oil, at least one emollient such as tridecyl stearate and a sunscreen mixture of at least two UV-B sunscreens and at least one UV-A sunscreen.

The sun protection factor (SPF) is a measure of the protection from the sun afforded by a sunscreen agent or composition containing same; compositions having higher SPF values afford more sun protection and are preferred. M. G. deNavarre discloses that small amounts (0.1 to 5 weight percent) of silicone oils can be used in suntan oils to make the oil film formed on the skin more water repellent. See for example The Chemistry and Manufacture of Cosmetics, 2nd Ed., 1975, Vol. III, Chapter 22, pp. 330 and 351 and Vol. IV, Chapter 39, pp. 667, 668 and 670-671; M. G. de Navarre, editor, Continental Press, Orlando Florida. However, there is no disclosure by deNavarre of any effect silicone oils may have on enhancing the SPF value of suntan compositions. In fact, deNavarre at p. 671 of Chapter 39, Vol. IV discloses creams and water-in-oil or oil-in-water lotions, not oils, are the preferred product types for use by people requiring maximum protection.

Dow Corning Corporation formulation sheets disclose two clear, waterproof sunscreen oils having SPF values of, respectively 8 and 15, which oils contain volatile silicone oils, ester emollients and a mixture of two sunscreens. However, the amounts of sunscreens in each formulation are too low to have SPF values approaching the reported SPF values.

Plough Inc. sells a high SPF-25 water proof sunscreen product containing volatile silicone oil but such product also contains waxes and as such is a stick product. Westwood Pharmaceutical sells a Presun SPF-29 UV-A/UV-B waterproof sunscreen product. The Westwood Pharmaceutical product is an emulsion product which contains water but does not contain any paraaminobenzoates (PABA) UV-B type sunscreening agents. There is still a need for a non-aqueous sunscreen oil composition which exists as an oil and has a high SPF.

SUMMARY OF THE INVENTION

The present invention provides a non-aqueous high-SPF sunscreen oil comprising at least one volatile oil selected from a volatile silicone oil, a volatile $C_{12}$–$C_{16}$ branched-chain hydrocarbon or mixtures thereof, at least one emollient selected from an ester of a straight or branched chain $C_{10}$–$C_{16}$ alcohol and a tri(loweralkyl) substituted benzoic acid, an ester of a straight or branched chain $C_{10}$–$C_{16}$ alcohol and a straight or branched-chain $C_4$–$C_{20}$ mono- or dicarboxylic acid, an ester of a branched-chain $C_5$–$C_{10}$ glycol and a straight or branched-chain $C_4$–$C_{20}$ mono- or dicarboxylic acid and mixtures thereof and a sunscreening effective amount of at least two UV-B sunscreens and at least one UV-A sunscreen.

The present invention also provides a non-aqueous high-SPF sunscreen oil comprising:

(a) about 20 to about 80 weight percent of at least one volatile oil selected from a volatile silicone oil, a volatile $C_{12}$–$C_{16}$ branched chain hydrocarbon and mixtures thereof;

(b) about 10 to about 50 weight percent of at least one emollient selected from an ester of a straight or branched chain $C_{10}$–$C_{16}$ alcohol and a tri(loweralkyl) substitutued benzoic acid, an ester of a straight or branched $C_{10}$–$C_{16}$ alcohol and a straight or branched chain $C_4$–$C_{20}$ mono- or dicarboxylic acid, an ester of branched chain $C_5$–$C_{10}$ glycol and a straight or branched chain $C_4$–$C_{20}$ mono- or dicarboxylic acid and mixtures thereof; and (c) about 10 to about 35 weight percent of a sunscreen mixture of at least two UV-B sunscreens and at least one UV-A sunscreen.

The present invention further provides a non-aqueous, high-SPF sunscreen oil comprising (a) about 35 to about 55 weight percent of at least one volatile oil selected from a volatile silicone oil, or a volatile $C_{12}$–$C_{16}$ branched-chain hydrocarbon and mixtures thereof;

(b) about 20 to about 40 weight percent of at least one emollient selected from an ester of a straight or branched-chain $C_{10}$–$C_{16}$ alcohol and a tri(loweralkyl)-substituted benzoic acid, an ester of a straight or branched-chain $C_{10}$–$C_{16}$ alcohol and a straight or branched chain $C_4$–$C_{20}$ mono- or dicarboxylic acid, an ester of branched-chain $C_5$–$C_{10}$ glycol and a straight or branched-chain $C_4$–$C_{20}$ mono- or dicarboxylic acid and mixtures thereof; and (c) about 16 to about 30 weight percent of a sunscreen mixture of at least one UV-A sunscreen and at least two UV-B sunscreens.

DETAILED DESCRIPTION OF THE INVENTION

The non-aqueous high SPF sunscreen compositions of the present invention exist as substantially clear oils at ambient temperatures and offer high sun protection factor (SPF) when applied topically. The non-aqueous high SPF sunscreen compositions are composed of lipophils, namely at least one volatile oil e.g. a volatile silicone oil or a volatile $C_{12}$ to $C_{16}$ branched hydrocarbon, at least one emollient such as tridecyl stearate and/or tridecyl trimellitate and a sunscreening amount of at least one UV-A sunscreen and at least two UV-B sunscreens and other components commonly used in sunscreens such as waterproofing agents, preservatives, antioxidants, colorants and fragrance. However, the lipophilic sunscreens composition of the present invention produce high SPF while being substantially free i.e. containing less than 1% by weight of cosmetic waxes such as ozokerite, carnauba wax and cetyl alcohol. In addition, the sunscreen compositions of the present invention do not contain mineral oil or film-forming cellulosic polymers such as cellulose ethyl ether which ethers lead to a hazy product. Thus, the lipohilic sunscreen compositions of the present invention are substantially clear oils, have a high SPF but do not contain prior art cosmetic waxes, or film-forming cellulosic polymers.

As used herein, the term "volatile silicone oil" means a silicone oil having a low heat of vaporization, i.e. normally less than about 50 cal per gram of silicone oil.

As used herein in reference to the compositions of the present invention, the term "non-aqueous" means substantially water-free. While water is not intentionally added to the compositions of the present invention, no attempt has been made to exclude or remove minute amounts of water from the ingredients used in the compositions of the present invention since it is not necessary that the compositions of the present invention be completely anhydrous. However, the equipment used in the preparation of the non-aqueous composition of the present invention are made completely dry before use.

As used herein in reference to the compositions of the present invention, the term "SPF" or "Sun Protection Factor" is defined in the Federal Register, Vol. 43, Aug. 25, 1978 Part 2, at page 38262, col. 1.

The term "high SPF" value as used herein means SPF value of at least 5, preferably at least 8, and includes SPF values of 5-25. As used herein the term "volatile oil" means volatile silicon oil as defined hereinabove and volatile $C_{12}$ to $C_{16}$ branched-chain hydrocarbons.

Typical suitable volatile silicone oils include cyclomethicones such as Dow Corning 344 Fluid, Dow Corning 345 Fluid, Dow Corning 244 Fluid and Dow Corning 245 Fluid; as well as Volatile Silicon 7207, a trademark of Union Carbide Corp., Danbury, Conn., low viscosity dimethicones i.e. dimethicones having a viscosity of about 50 cst or less, especially dimethicones, such as, Dow Corning 200-0.5 cst Fluid. The Dow Corning Fluids are available from Dow Corning Corporation, Midland, Mich. 48640. Cyclomethicone and dimethicone are names given by the Third Edition of the CTFA Cosmetic Ingredient Dictionary to cyclic dimethyl polysiloxane compounds and a mixture of fully methylated linear siloxane polymers end-blocked with trimethylsiloxy units, respectively. Other volatile silicone oils having a low heat of vaporization such as those available from General Electric, Co., Silicone Products Div., Waterford, N.Y. and SWS Silivones Div. of Stauffer Chemical Co., Adrian, Mich., can also be used in the compositions of the invention.

As used herein, the term "volatile $C_{12}$-$C_{16}$ branched chain hydrocarbon" means $C_{12}$-$C_{16}$ branched-chain hydrocarbons having a boiling of no more than about 250° C. and preferably in range of from about 178 to about 250° C. at atmospheric pressure. Typical suitable volatile $C_{12}$ to $C_{16}$ branched chain hydrocarbons include iso-dodecane sec-dodecane, tert-dodecane, iso-, sec-, and tert-tridecane, iso-, sec- and tert-tetradecane, iso-, sec- and tert-pentadecane and iso-, sec- and tert-hexadecane. Preferred volatile $C_{12}$-$C_{16}$ branched-chain hydrocarbons are isododecane such as is available under the tradename Permethyl 99A from Permethyl Corp., Frazer, Pa. and iso-hexadecane such as is available from the Permethyl Corp. under the tradename Permethyl 101A.

Typical suitable emollients include esters of a straight or branched-chain $C_{10}$-$C_{16}$ alcohol and a straight or branched chain $C_4$-$C_{20}$ mono- and dicarboxylic acids and esters of a straight or branched-chain $C_{10}$-$C_{16}$ alcohol and a tri(loweralkyl) substituted benzoic acid. Typical suitable straight and branched-chain $C_{10}$-$C_{16}$ alcohols include n, sec-, iso- and tert-decanol, n, sec- iso- and tert-undecanol, n-, sec- iso- and tert-dodecanol, n-, sec- iso- and tert-tridecanol, n-, sec- tri- and tert-tetradecanol, n-, sec-, iso-, and tert-pentadecanol and n-, sec-, iso- and tert-hexadecanol. Preferred branched and straight chain $C_{10}$-$C_{16}$ alcohols are n-decanol, isodecanol, n-tridecanol iso-tridecanol and iso-pentadecanol.

Typical suitable branched-chain $C_5$-$C_{10}$ glycols include neopentyl glycol and pentaerythritol.

The preferred esters of branched-chain $C_5$-$C_{10}$ glycols and $C_4$-$C_{20}$ monocarboxylic acids are the diester of neopentyl glycol and decanoic acid, (neopentyl glycol dicaprate), the diester of neopentyl glycol and octanoic acid, (neopentyl glycol dicaprylate) and the diester of neopentyl glycol and 2-ethylhexanoic acid.

Typical suitable straight and branched-chain $C_4$-$C_{20}$ mono- and dicarboxylic acids include the straight and branched chain monocarboxylic acids substituted by hydroxy or double bonds including monocarboxylic acids such as: butanoic, pentanoic, 2-methyl- and 3-methyl-pentanoic, 2,2-dimethylpropanoic, hexanoic, 2-methyl-, 3-methyl-, and 4-methylhexanoic, 2-ethylbutanoic, 2,2dimethylbutanoic, heptanoic, 2-methyl-, 3-methyl-, 4-methyl-, 5-methyl- and 6-methyl -heptanoic, 2-ethylhexanoic, octanoic (caprylic), 2-methyl-, 3-methyl-, 4-methyl-, 5-methyl-, 6-methyl- and 7-methyloctanoic, nonanoic, 2-methyl-, 3-methyl-, 4-methyl-, 5-methyl-, 6-methyl-, 7-methyl- and 8-methylnonanoic, 3,3,5trimethylhexanoic (isonanonic), decanoic (caproic), 2-methyl-, 3-methyl-, 4-methyl-, 5-methyl-, 6-methyl-, 7-methyl-, 8-methyl-, 9-methyldecanoic, undecanoic, dodecanoic (lauric), dineopentylacetic, methyl-t-butylneopentylacetic, tridecanoic, tetradecanoic (myristic), pentadecanoic, hexadecanoic (palmitic), heptadecanoic (margaric), octadecanoic (stearic), hydroxystearic 16-methylheptadecanoic (isostearic), double bond substituted (unsaturated) carboxylic acids such as oleic(cis-9-octadecenoic), linoleic (cis,cis-9,12-octadecadienoic) and linolenic cis,cis,cis-9,12,15-octadecatrienoic acid), nonadecanioc and $CH_3(CH_2)_{18}CO_2H$.

Typical suitable $C_4$-$C_{20}$ dicarboxylic acids include dicarboxylic acids of the formula $(CH_2)_n(CO_2H)_2$ wherein n is 2 to 18 including succinic (n=2), glutaric (n=3), adipic (n=4), pimelic (n=5), suberic (n=6), azelaic (n=7), sebacic (n=8) as well as the $C_{13}$, $C_{16}$ and $C_{19}$ members such as Brassilic ($C_{13}$), thapsic ($C_{16}$) and nonadecance-1,19-dicarboxylic acid. The preferred dicarboxylic acids are succinic and adipic.

Typically suitable tri(lower alkyl) substituted benzoic acid include tri-methylbenzoic acids, such as 1,1,3-trimthylbenzoic acid, 1,2,4-trimethyl-benzoic acid (trimellitic acid), and 1,3,5-trimethylbenzoic acid (trimesic acid). The preferred tri(loweralkyl)benzoic acid is trimellitic acid.

Preferred esters of $C_4$ to $C_{20}$ monocarboxylic acids and straight and branched chain $C_{10}$-$C_{16}$ alcohols include tridecyl neopentonate, isotridecyl isononanoate, isodecyl neopentonate, isodecyl hydroxystearate, isodecyl laurate, isodecyl myristate, isodecyl oleate, isodecyl palmitate, decyl oleate, and isocetyl palmitate (isohexadecyl hexadecanoate) and iso-hexadecyl isodecanoate (14-methylpentadecyl-8-methylnonanoate).

The preferred esters of straight and branched-chain $C_{10}$-$C_{16}$ alcohols and $C_4$-$C_{20}$ dicarboxylic acids is decyl succinate. The preferred esters of straight and branched-chain $C_{10}$-$C_{16}$ esters of tri(loweralkyl) substituted benzoic acids are the decyl, isodecyl, isotridecyl and tridecyl esters of trimethylbenzoic acids especially trimellitic acid; tridecyl trimellitate is more preferred.

In a preferred embodiment of this invention, the emollient is a mixture of tridecyl trimellitate and tridecyl stearate In another preferred embodiment, the emollient is a mixture of tridecyl trimellitate, tridecyl stearate, neopentyl glycol dicaprylate and neopentyl dicaprate such as is available from Lipo Chemicals Inc., Patterson, N.J. under the tradename Lipovol MOS-70.

The compositions of the present invention all contain a sunscreening effective amount of a combination of oil-soluble sunscreening agents of at least two UV-B types and at least one UV-A type. UV-A type sunscreening agents protect against long wavelength actinic radiation in the 320 to 400 nm range and UV-B sunscreening agents protect against shorter wavelength, actinic radiation in the 290-320 nm range.

Typical suitable UV-B type sunscreening agents include substituted para-aminobenzoates, e.g., octyl dimethyl PABA, available from Van Dyk & Co., Inc., Belleville, N.J. 07109 under the tradename Escalol 507 and usually present in the range of about 1.5 to 8.0 weight percent, alkyl esters of para-methoxycinnamate, e.g., octyl para-methoxycinnamate, available from Givaudan Corp., Clifton, N.J. 07104 under the tradename Parsol MCX and usually present in the range of about 1.5–7.5 weight percent, certain esters of salicylic acid, e.g., homomenthyl salicylate, usually in the range of about 4.0 to 15 weight percent or octyl salicylate, usually in the range of about 3 to 5 weight percent. (All weight percents are weight percent of total sunscreen composition).

Typical suitable UV-A type sunscreening agents include benzophenone-3 usually present in the composition in the range of about 0.5 to 6 percent and available from American Cyanamid Co., Wayne, N.J. 07470 under the tradename Spectra-Sorb UV-9 and benzophenone-8, usually present in the composition in the range of about 0.5 to 3 weight percent and available from American Cyanamid Co. under the tradename Spectra-Sorb UV-24 and menthyl anthranilate, usually present in the composition in the range of about 3.5 to about 5.0 weight percent and available from Felton International, Inc. Brooklyn, N.J. under the tradename Sunarome UVA.

The compositions of the present invention preferably contain a combination of at least two UV-B type sunscreening agents and one UV-A type sunscreening agent.

The compositions of the present invention may also contain perfumes preservatives dyes colorants, softeners, waterproofing agents, and antioxidants as well as any other class of materials whose presence may be cosmetically, or otherwise desirable.

Typical suitable antioxidants include propyl, octyl and dodecyl esters of gallic acid, butylated hydroxyanisole (usually as a mixture of ortho and meta isomers), butylated hydroxytoluene and nordihydroguaiaretic acid.

Typical suitable preservatives include the lower alkyl esters of para-hydroxybenzoates (parabens) especially, methyl paraben, ethyl paraben, propyl paraben, butyl paraben, isobutyl paraben and mixtures thereof, and benzoic acid.

Typical suitable perfumes include any oil soluble perfume or fragrance or mixture of perfumes or fragrances well known to those skilled in the art.

The non-aqueous sunscreen compositions of the present invention also may include a waterproofing effective amount at least one waterproofing agent.

By the term "waterproofing effective amount of at least one waterproofing agent" means the waterproofing agent(s) is present in the compositions of the present invention at a concentration of about 0.01 to about 10.0 weight percent, preferably about 1.0 to about 10.0 percent.

Typical suitable waterproofing agents include copolymers derived from polymerization of octadecene-1 and maleic anhydride in accordance with the published procedures such as those in U.S. Pat. No. 3,860,700 and Reissue No. 28,475. The preferred waterproofing agent is a copolymer commercially available from Chevron Chemicals Co. under the tradename, PA-18 polyanhydride resin.

The volatile oil component makes up about 20 to about 80 weight percent, preferably about 35 to about 55 weight percent of the non-aqueous sunscreen composition.

The emollient component makes up about 10 to about 50 weight percent, preferably about 20 to about 40 weight of the non-aqueous sunscreen composition.

The sunscreens account for about 10 to about 35 weight percent, preferably about 12 to about 30 weight percent of the non-aqueous sunscreen composition. A preferred non-aqueous sunscreen composition of this invention having an SPF value of about 8 contains about 16 to 18 weight percent of a combination of at least two UV-B sunscreens and one UV-A sunscreen. Another preferred non-aqueous sunscreen composition of this invention having an SPF value of about 15 contains about 26 to about 28 weight percent of a combination of at least two UV-B sunscreens and one UV-A sunscreen.

Definitions and suppliers of the ingredients used in the following illustrative examples may be found in the CTFA Cosmetic Ingredient Dictionary, published by the Cosmetic, Toiletry and Fragrance Association, Inc., 1110 Vermont Avenue, NW, Wash. D.C. 20005, Third Edition, 1982. All proportions are by percent weight.

EXAMPLE 1

| Non-Aqueous Sunscreen Oil SPF 15 | |
|---|---|
| Ingredients | Weight Percent |
| Part A | |
| Lipovol MOS-70* | 30.0 |
| Benzoic Acid | 0.2 |
| Propyl Paraben | 0.1 |
| Octyl Dimethyl PABA | 8.0 |
| Benzophenone-3 | 6.0 |
| Homomenthyl Salicylate | 5.0 |
| Octyl p-methoxycinnamate | 7.5 |
| Part B | |
| Octadecene-1/Maleic Anhydride | 3.0 |
| Part C | |
| Dow Corning Silicone Fluid DC 344 | 38.7 |
| Fragrance | 1.5 |
| Total | 100.0 |

*Available from Lipo Chemicals Co., Paterson, New Jersey

Admix the ingredients in Part A in a stainless steel pot at a temperature of 82° C. equipped with a stirrer until a homogeneous admixture is formed. Slowly admix the ingredient in Part B to Part A, until a homogeneous admixture is formed. Cool the admixture of A and B to 38° C. Admix Part C to the admixture of Parts A and B until a homogeneous admixture is formed. The static SPF value of the admixture was measured to be 15. The admixture is expected to be water-resistant.

EXAMPLE 2

| Non-Aqueous Sunscreen Oil SPF 8 | |
|---|---|
| Ingredients | Weight Percent |
| Part A | |
| Lipovol MOS-70 | 30.0 |
| Benzoic Acid | 0.2 |
| Propyl Paraben | 0.1 |

-continued

| Non-Aqueous Sunscreen Oil SPF 8 | |
|---|---|
| Ingredients | Weight Percent |
| Octyl Dimethyl PABA | 8.0 |
| Benzophenone-3 | 4.0 |
| Homomenthyl Salicylate | 5.0 |
| Part B | |
| Octadecene-1/Maleic Anhydride | 3.0 |
| Part C | |
| Dow Corning Silicone Fluid DC 344 | 48.2 |
| Fragrance | 1.5 |
| Total | 100.0 |

Follow the procedure of Example 1 to produce a water-resistant non-aqueous sunscreen oil having a static SPF value of 8.

What is claimed is:

1. A non-aqueous high-SPF sunscreen oil comprising:
   (a) about 20 to about 80 weight percent of at least one volatile oil selected from the group consisting of a volatile silicone oil, a volatile $C_{12}$–$C_{16}$ branched-chain hydrocarbon and mixtures thereof:
   (b) about 10 to about 50 weight percent of at least one emollient selected from the group consisting of an ester of a straight or branched-chain $C_{10}$–$C_{16}$ alcohol and a tri(loweralkyl) substituted benzoic acid, an ester of a straight or branched $C_{10}$–$C_{16}$ alcohol and a straight or branched chain $C_4$–$C_{20}$ mono- or dicarboxylic acid, an ester of a branched-chain $C_5$–$C_{10}$ glycol and a straight or branched-chain $C_4$–$C_{20}$ mono- or dicarboxylic acid and mixtures thereof; and
   (c) about 10 to about 35 weight percent of a sunscreen mixture of at least two UV-B sunscreens and at least one UV-A sunscreen.

2. A non-aqueous, high-SPF sunscreen of claim 1 wherein the volatile oil is a volatile silicone oil.

3. A non-aqueous, high-SPF sunscreen of claim 1 wherein the volatile oil is a $C_{12}$ branched-chain hydrocarbon.

4. A non-aqueous, high-SPF sunscreen of claim 1 wherein the one of the emollients is tridecyl stearate.

5. A non-aqueous, high-SPF sunscreen oil of claim 1 wherein the $C_{10}$–$C_{16}$ alcohol moiety of one of the esters is tridecyl.

6. A non-aqueous, high-SPF sunscreen of claim 1 wherein and $C_{10}$–$C_{16}$ alcohol moiety is selected from the group consisting: of n-decanol, isodecanol, n-tridecanol, iso-tridecanol and iso-pentadecanol.

7. A non-aqueous, high-SPF sunscreen of claim 2 wherein said volatile silicone oil is selected from the group consisting of: cyclomethicones, and low viscosity demithicones having a viscosity of about 50 cst or less.

8. A non-aqueous, high-SPF sunscreen of claim 1 wherein said ester is selected from the group consisting of:
   (1) esters of branched-chain $C_5$–$C_{10}$ glycols and $C_4$–$C_{20}$ monocarboxylic acids selected from the group consisting of:
      (a) the diester of neopentyl glycol and decanoic acid,
      (b) the diester of neopentyl glycol and octanoic acid, and
      (c) the diester of neopentyl glycol and 2-ethylhexanoic acid;
   (2) esters of $C_4$–$C_{20}$ monocarboxylic acids and straight and branched-chain $C_{10}$–$C_{16}$ alcohols selected from the group consisting of:
      (a) tridecyl neopentonate,
      (b) isotridecyl isononanoate,
      (c) isodecyl neopentonate,
      (d) isodecyl hydroxystearate,
      (e) isodecyl laurate,
      (f) isodecyl myristate,
      (g) isodecyl oleate,
      (h) isodecyl palmitate,
      (i) decyl oleate,
      (j) isocetyl palmitate, and
      (k) isohexaecyl isodecanoate;
   (3) esters of straight and branched-chain $C_{10}$–$C_{16}$ esters of tri(loweralkyl) substituted benzoic acids selected from the group consisting of: the decyl, isodecyl, isotridecyl an tridecyl esters of trimethylbenzoic acids:
   (4) a mixture of tridecyl trimellitate and tridecyl stearate; and
   (5) a mixture of tridecyl trimellitate, tridecyl stearate, neopentyl glycol dicaprylate and neopentyl dicaprate.

9. A non-aqueous high-SPF sunscreen of claim 1 wherein said ester of said tri(loweralkyl)substituted benzoic acid is tridecyl trimellitate.

10. A non-aqueous high-SPF sunscreen of claim 8 wherein said ester is a mixture of tridecyl trimellitate, tridecyl stearate, neopentyl glycol dicaprylate and neopentyl dicaprate.

11. A non-aqueous high-SPF sunscreen of claim 10 wherein the volatile oil is a cyclomethicone silicone oil.

12. A non-aqueous, high-SPF sunscreen oil comprising:
   (a) about 35 to about 55 weight percent of at least one volatile oil selected from the groups consisting of a volatile silicone oil, a volatile $C_{12}$–$C_{16}$ branched-chain hydrocarbon and mixtures thereof;
   (b) about 20 to about 40 weight percent of at least one emollient selected from the group consisting of an ester of a straight or branched-chain $C_{10}$ to $C_{16}$ alcohol and a tri(loweralkyl) substituted benzoic acid, an ester of a straight or branched-chain $C_{10}$–$C_{16}$ alcohol and a straight or branched-chain $C_4$–$C_{20}$ mono- or dicarboxylic acid, an ester of a branched-chain $C_5$–$C_{10}$ glycol and a $C_4$–$C_{20}$ mono- or dicarboxylic acid and mixtures thereof; and
   (c) about 16 to about 30 weight percent of a sunscreen mixture of at least one UV-A sunscreen and at least two UV-B sunscreens.

13. A non-aqueous high-SPF sunscreen oil of claim 12 wherein sunscreen mixture is a mixture of one UV-A and at least two UV-B sunscreens in an amount of about 16 to about 18 weight percent of said sunscreen oil.

14. A non-aqueous, high-SPF sunscreen of claim 12 wherein the sunscreen mixture is a mixture of at least one UV-A sunscreen and at least two UV-B sunscreens in an amount of about 26–28 weight percent of said sunscreen oil.

15. A non-aqueous, high-SPF sunscreen of claim 12 wherein the volatile oil is a volatile silicon oil in an amount of about 35 to 45 weight percent of said sunscreen.

16. A non-aqueous, high-SPF sunscreen oil of claim 12 wherein the emollient is a mixture of esters of tridecanol in an amount of about 30 weight percent of said sunscreen oil.

17. A non-aqueous, high-SPF sunscreen oil of claim 12 wherein the emollient is a mixture of a tridecyl ester of a $C_{16}$–$C_{18}$ monocarboxylic acid and a tridecyl ester of a tri(loweralkyl) benzoic acid in an amount of about 20 to about 40 weight percent of said sunscreen oil.

18. A non-aqueous, high SPF sunscreen oil of claim 12 wherein the emollient is a mixture of tridecyl ester of a $C_{16}$–$C_{18}$ monocarboxylic acid, a tridecyl ester of a tri(loweralkyl)benzoic acid, a diester of neopentyl glycol and decanoic acid and a diester of neopentyl glycol and octanoic acid in an amount of about 20 to about 40 weight percent of said sunscreen oil.

* * * * *